United States Patent [19]

Teng et al.

[11] Patent Number: 5,750,681
[45] Date of Patent: May 12, 1998

[54] BICYCLIC BETA-LACTAMS AND PROCESS THEREFOR

[75] Inventors: Min Teng, Aliso Viego, Calif.; Marvin J. Miller, South Bend, Ind.

[73] Assignee: University of Notre Dame Du Lac, Notre Dame, Ind.

[21] Appl. No.: 491,821

[22] Filed: Jun. 19, 1995

[51] Int. Cl.$^6$ .................................................. C07D 207/00
[52] U.S. Cl. ............................................................ 540/203
[58] Field of Search ............................................. 540/203

[56] References Cited

U.S. PATENT DOCUMENTS

| | | | |
|---|---|---|---|
| 4,885,362 | 12/1989 | Morin, Jr. et al. | 540/364 |
| 4,892,942 | 1/1990 | Munro | 540/205 |
| 5,250,676 | 10/1993 | Gasparski et al. | 540/200 |

FOREIGN PATENT DOCUMENTS 0 508 234   10/1992   European Pat. Off. .

OTHER PUBLICATIONS

Guzzo, Teng, Miller, Tetrahedron vol. 50, pp. 8275–8292, Jul. 1994.

M. Teng M.J. Miller, J. Am. Chem. Soc. No. 2, pp. 548–554, Jan. 1993.

*Primary Examiner*—Jeffrey Mullis
*Attorney, Agent, or Firm*—William B. Scanlon

[57] ABSTRACT

Bicyclic β-lactams comprising a 5- or 6-membered lactone or lactam ring are obtained in a process comprising a base induced intramolecular cyclization of a 4-substututed β-lactam having a leaving group in the 1-position. An intramolecular nucleophile transfer reaction is proposed as the operative mechanism and the bicyclic β-lactams are obtained in the required stereochemical form for biological activity. The compounds provided are useful intermediates for the preparation of antibiotics and β-lactamase inhibitors.

7 Claims, No Drawings

BICYCLIC BETA-LACTAMS AND PROCESS THEREFOR

BACKGROUND OF THE INVENTION

This invention relates to β-lactam compounds. In particular, it relates to bicyclic β-lactam compounds wherein the 4-membered β-lactam ring is fused in the 3,4-position to a 5- or 6-membered lactone or lactam ring. In a further aspect of the invention, there is provided a process for preparing the bicyclic β-lactams which comprises an intramolecular nucleophile transfer reaction of a substituted β-lactam during which the fused second lactone or lactam ring is formed.

The β-lactam ring forms part of the molecular structure of the β-lactam antibiotics, notably the penicillins and the cephalosporins, as well as numerous other antibiotics and β-lactamase inhibitors.

New and improved antibiotics are constantly being pursued by researchers because of the ability of bacteria to develop resistance to the current variety of antibiotics. This is particularly true of the β-lactam antibiotics. Bacteria develop resistance to some of these antibiotics by developing the ability to produce protective β-lactamase which are able to destroy or diminish the activity of the antibiotic in the bacteria's environment.

An intermolecular process for preparing 3-substituted β-lactams is described in U.S. Pat No. 5,250,676 issued to Gasparski, Miller and Teng. Also, Biswas and Miller report the rearrangement of N-(toluenesulfonyloxy) 2-pyrrolidone in *Heterocycles*, 26, No. 11, 2849 (1987). The inventors herein have published preliminary work on the intramolecular transfer process in *Tetrahedron* Vol. 50, No. 28, pp. 8275–8292, 1994.

DETAILED DESCRIPTION

The bicyclic β-lactam compounds provided by the invention are represented by the structural formula 1

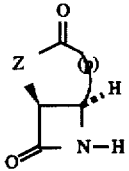

1 wherein Z is —O— or —N—J wherein J is —OC(O)R, —P(O)(OR$_1$)(OR$_1$'), or —SO$_2$R$_2$; wherein R is $C_1$–$C_4$ alkyl, R$_1$ and R$_1$' independently are $C_1$–$C_4$-alkyl, phenyl or substituted phenyl; R$_2$ is $C_1$–$C_4$-alkyl, phenyl, substituted phenyl, naphthyl or substituted naphthyl; and p is —CH$_2$—, —CH$_2$—CH$_2$—, cis-CH=CH—, —CH(alk)—, —CH$_2$—CH(alk), or —CH(alk)—CH$_2$—wherein alk is methyl or ethyl.

The terms used in the formula 1 have the following meanings. The term "$C_1$–$C_4$-alkyl" refers to methyl, ethyl, n-propyl, iso-propyl, n-butyl, t-butyl, iso-butyl, and sec-butyl. "Substituted phenyl" refers to phenyl mono- or disubstituted by $C_1$–$C_4$-alkyl, halogen, $C_1$–$C_4$-alkoxy, hydroxy, nitro, trifluoromethyl, cyano, carboxy, or carboxamido, and when disubstituted such groups may be the same or different. Examples of mono- and disubstituted phenyl moieties are 4-methylphenyl, 3,4-dimethylphenyl, 2,4-dimethylphenyl, 4-ethylphenyl, 4-t-butylphenyl, 3-methyl-4-ethylphenyl, 2,4-dichlorophenyl, 4-chlorophenyl, 3-methyl-4-chlorophenyl, 4-bromophenyl, 4-fluorophenyl, 4-hydroxyphenyl, 3-chloro-4-hydroxyphenyl, 3,4-methylenedioxyphenyl, 4-methyl-3-hydroxyphenyl, 2,4-dihydroxyphenyl, 4-trifluoromethylphenyl, 4-nitrophenyl, 3-nitrophenyl, 2,4-dinitrophenyl, 3-methoxyphenyl, 4-ethoxyphenyl, 4-carboxyphenyl, 3-hydroxy-4-carboxyphenyl, 4-carboxamidophenyl, 3-cyanophenyl, and like mono- and disubstituted phenyl groups; "naphthyl" refers to 1-naphthyl and 2-naphthyl; "substituted naphthyl" refers to 1- or 2-naphthyl mono-or disubstituted by $C_1$–$C_4$-alkyl, halogen, hydroxy, $C_1$–$C_4$-alkoxy, carboxy, carboxamido, cyano, trifluoromethyl, or nitro and, when 1- or 2-naphthyl is disubstituted such substituents may be the same or different. Examples of substituted naphthyl groups are 4-hydroxy-2-naphthyl, 8-hydroxy-2-naphthyl, 6-chloro-1-naphthyl, 6-chloro-2-naphthyl, 4-methyl-2-naphthyl, 4,6-dimethyl-2-naphthyl, 7-cyano-2-naphthyl, 4-carboxy-1-naphthyl, 8-chloro-2-naphthyl, 4-nitro-2-naphthyl, 4-trifluoromethyl-2-naphthyl, 8-methoxy-2-naphthyl, 4-chloro-8-ethoxy-2-naphthyl, and like mono- and disubstituted naphthyl groups.

As is shown in the formula 1 the compounds have the cis configuration at the 3,4-positions of the ring juncture. This stereo configuration is that possessed by many biologically active β-lactam antibiotics, especially bicyclic β-lactam antibiotics and for many of the β-lactamase inhibitors which have the β-lactam ring structure. The cis configuration of the compounds of formula 1 is obtained in the process of the invention as described hereinafter.

The following are examples of compounds of the invention where, in formula 1, Z is —O—: 2-oxa-7-azabicyclo[4.2.0.]octane, 3,8-dioxo, 2-oxa-6-6-azabicyclo[3.2.0.] heptane, 3,7-dioxo, and 2-oxa-7-azabicyclo[4.2.0]octane, 4-methyl-3,8-dioxo, which are represented respectively by the formulas 2, 3, and 4.

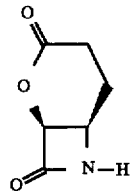

2

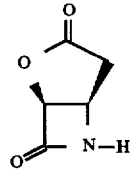

3

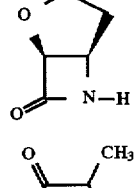

4

Examples of compounds represented by formula 1 wherein Z is =N—J are 2,7-diazabicyclo[4.2.0.]octane, 3,8-dioxo-2-(2,2-dimethyl-1-oxopropoxy), 2,7-diazabicyclo[4.2.0.]octane, 3,8-dioxo-2-diphenoxyphosphoramide, 2,7,-diazabicyclo[4.2.0.]octane, 3,8-dioxo-2-diethoxyphosphoramide, and 2,7-diazabicyclo[4.2.0.] octane, 3,8-dioxo-2-[(4-methylphenyl)sulfonyloxy]. The above named compounds are represented by the following formula 5

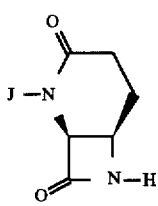

wherein J is respectively CH₃C(CH₃)₂C(O)—O—, (C₆H₅O)₂—P(O)—, (C₂H₅O)₂P(O)—, and tosyloxy.

Certain of the compounds represented by the formula 1 are preferred over others. Preferred compounds of the invention are represented by the formula 1 wherein Z is the group =N—J wherein J is —OC(O)R, —SO₂—R₂ or —P(O)(OR₁)(OR₁'). Of the preferred compounds those represented wherein p is —CH₂— or —CH₂CH₂— are especially preferred. Among the compounds wherein J is —O(CO)R the preferred are represented when R is a t-butyl group. Among the compounds wherein J is —SO₂—R₂ further preferred compounds are those wherein R₂ is 4-methylphenyl or 1- or 2-naphthyl. Among the preferred compounds wherein J is —P(O)(OR₁)(OR₁') especially preferred compounds are represented when R₁ and R₁' are both phenyl or 4-chlorophenyl, and when R₁ is C₁–C₃ alkyl and R₁' phenyl or 4-chlorophenyl.

The compounds provided by the invention are prepared via an intramolecular cyclization of a compound represented by the formula 6

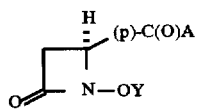

wherein A is —OH or —NH—J, and wherein p, and J have the same meanings as defined for formula 1 and Y—O— represents a leaving group wherein Y is the acyl residue of an organic acid having a pKa of less than about 3.

The process is carried out by mixing a compound of the formula 6 in an inert aprotic solvent with a tert-amine or with a highly hindered sec-amine. The reaction proceeds at a temperature between about –40° C. to about 55° C. and preferably at or about room temperatures. The mixture is provided with good agitation such as stirring or shaking and the progress of the process can be monitored via thin layer chromatography or HPLC with small aliquots of the mixture taken from time to time.

The product (formula 1) is recovered from the reaction mixture and is separated from side products by employing conventional methods such as HPLC and stepwise or gradient elution chromatography.

The leaving group moiety, —OY, in the 1-position of the β-lactam shown by formula 6 is obtained by reacting the 1-hydroxy substituted β-lactam with the acid YOH preferably in the form of an activated derivative such as the acid halide or an active ester or anhydride derivative. Examples of acids which can be used to form the leaving group are the arylsulfonic acids such as benzesulfonic acid, toluenesulfonic acid, 1- or 2-naphthlenesulfonic acid, 4-chlorobenzenesulfonic acid, 2,4-dichlorobenzenesulfonic acid, and 4-fluorobenzenesulfonic acid; the alkylsulfonic acids such as, for example, methanesulfonic acid, ethanesulfonic acid, and butanesulfonic acid; the phosphonic acids such as, for example, the dialkyl and diphenylphosphates such as diethylphosphate, dipropylphosphate, dimethylphosphate, diphenylphosphate, di-(4-chlorophenyl) phosphate, and mixed alkyl aryl phosphates such as ethylphenylphosphate.

Preferred leaving groups of the invention are represented by the term —OY wherein Y is —S(O)₂Y' wherein Y' is phenyl, substituted phenyl naphthyl or substituted naphthyl. An especially preferred Y' group is the p-toluenesulfonyl (tosyl) group. Another group of —OY leaving groups is represented when Y is the group —P(O)(OR₁)(OR₁') wherein R₁ and R₁' are phenyl or substituted phenyl.

Tertiary amine bases which can be used in the process are non-nucleophilic acid scavenging amines having a base strength of approximately pK of 10. Examples of such bases are triethylamine, tripropylamine, methyldiethylamine, diisopropylethylamine (DIEA), dimethylcyclopentylamine, 4-dimethylaminopyridine (DMAP) and like tertiary amine bases. Preferably the amine is sterically hindered such as is a preferred amine base of the invention, DIEA. Highly hindered secondary amines may also be used for example di-t-butylamine and dicyclohexylamine.

The amount of base used in the process may vary from about two equivalents to an excess of about twenty equivalents or more per starting material (formula 6) used in the process. When A of the starting material 6 is the group —NHJ the hydrogen atom attached to the nitrogen exhibits a pK$_a$ of less than about 9 and preferably less than about 7. In general, a higher ratio of base to starting material is used in the process when the pK$_a$ of such starting material is less than about 7.

Aprotic solvents which can be used in the process are organic solvents such as, for example, the alkyl nitriles acetonitrile and propionitrile; ethers such as tetrahydofuran, tetrahydropyran, dioxane and 1,2-dimethoxyethane; chlorinated hydrocarbons such as methylene chloride, 2,2,2-trichloroethane, 1,2,2-trichloroethane and like aprotic solvents. The choice of aprotic solvent is not critical as long as it serves to solubilize the starting material and the base at sufficient concentration levels to allow the process to proceed.

For best results the process is carried out under anhydrous conditions although rigid exclusion of water is unnecessary since the process tolerates spurious amounts of water.

While not intending to bound by any particular reaction mechanism by which the process may proceed a plausible mechanism comprises a nucleophilic transfer reaction wherein the nucleophile group of the 4-position substituent on the β-lactam (A of formula 6) displaces the leaving group on the β-lactam ring nitrogen after formation of a transitory enol intermediate generated by the base employed in the process. The mechanism is illustrated by the following general reaction scheme wherein LG represents the leaving group and Nu represents the nucleophile.

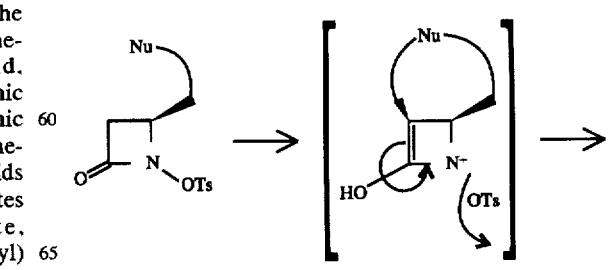

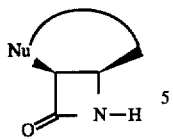

The bicyclic β-lactam products of the process are often accompanied by significant amounts of side products most likely formed by competing routes. The nature of the side products derives from the particular starting material used in the process. The side products are noted below in the specific embodiments as well as in the specific examples provided hereinafter.

A specific embodiment of the process of the invention comprises mixing at room temperature a compound represented by the formula 6 wherein, p is —CH₂CH₂—, A is OH and Y is toluenesulfonyl, in acetonitrile with about 2 equivalents of DIEA to provide 2-oxa-7-azabicyclo[4.2.0.]octane, 3,8-dioxo, (2) represented by the formula 1 wherein Z is —O—, and p is —CH₂CH₂—. The embodiment is shown in the following reaction scheme

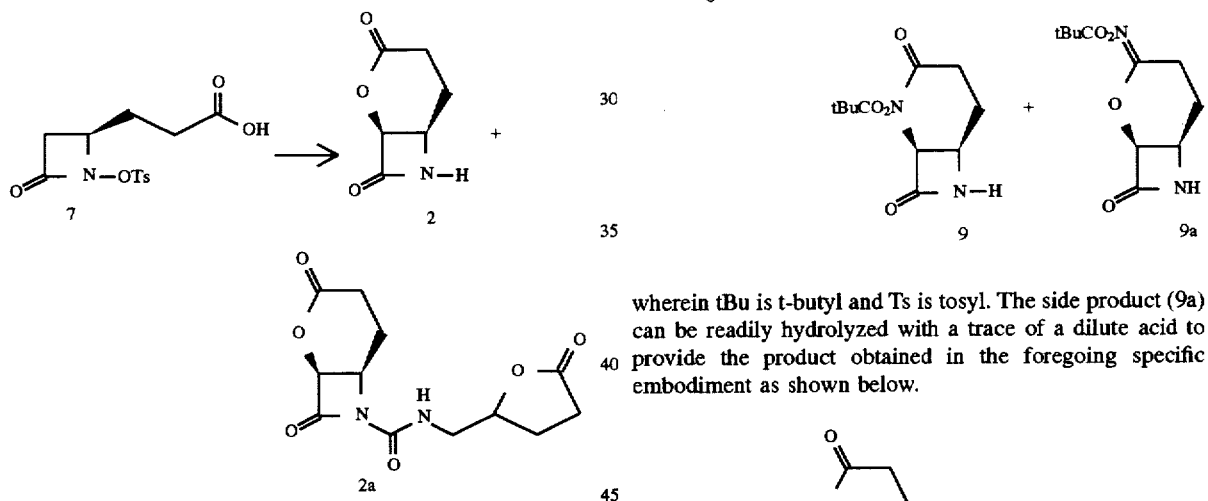

wherein Ts is tosyl. The side product (2a) is likely formed by a competing Lossen rearrangement involving the starting material followed by N-acylation of the product with an isocyanate as shown below.

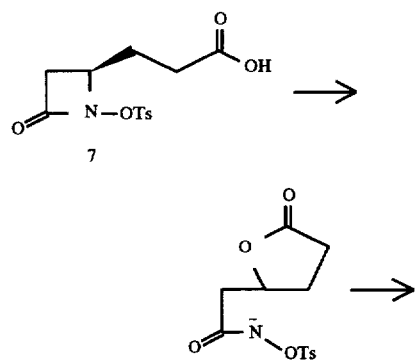

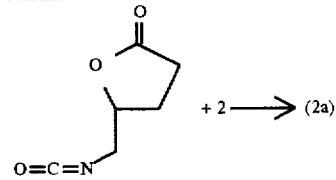

Another embodiment of the process comprises mixing at ambient temperature 2-azetidinepropanamide, N-(2,2-dimethyl-3-oxopropoxy)-1-[[(4-methylphenyl)sulfonyl]oxy]-4-oxo, (8) in acetonitrile with 2 equivalents of DIEA to yield a 1:1 mixture of 2,7-diazabicyclo[4.2.0.]octane, 3,8-dioxo-2-(2,2-dimethyl-1-oxopropoxy) (9) and the side product 2-oxa-7-azabicyclo[4.2.0.]octane, 3-[imino(2,2-dimethyl-1-oxopropoxy)]-8-oxo, (9a) as shown in the following reaction scheme

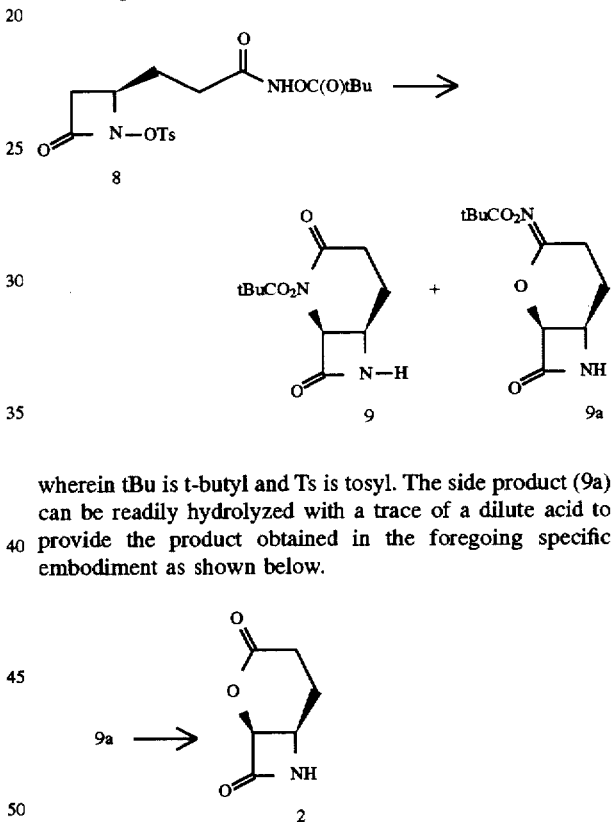

wherein tBu is t-butyl and Ts is tosyl. The side product (9a) can be readily hydrolyzed with a trace of a dilute acid to provide the product obtained in the foregoing specific embodiment as shown below.

A further specific embodiment comprises mixing in acetonitrile at ambient temperature 2-azetidinepropanamide, N-(diphenoxyphosphoramidic)-1-[[(4-methylphenyl)sulfonyl]oxy]-4-oxo (10), with DIEA for about 45h, to yield 2,7-diazabyclo[4.2.0.]octane, 3,8-dioxo-2-diphenoxyphosphoramide, (11) as shown below.

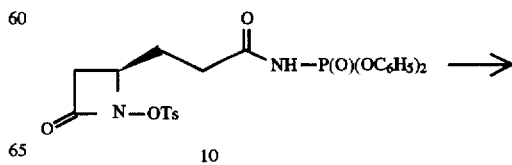

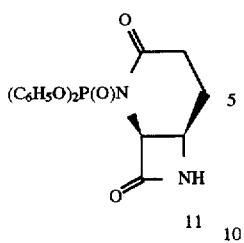

The starting materials represented by the formula 6 are obtained as follows. The carboxylic acid compounds represented by the formula 6 wherein A is OH are prepared as described by Guzzo, P. R.; Miller, M. J. *Journal of Organic Chemistry* 1994, 59, 4862–4867. For example, the β-lactam t-butyl ester represented by the formula 12

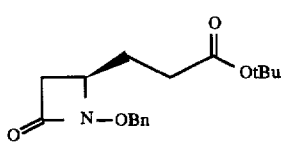

wherein tBu is benzyl is deesterifed with trifluoroacetic acid and anisole to provide the free acid 13.

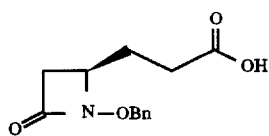

The benzyl group is removed by catalytic hydrogenolysis over palladium on carbon to yield the N-hydroxy free acid compound. Treatment of the N-hydroxy β-lactam free acid with tosyl chloride, napsyl chloride or other activated Y group provided the N—OY substituted β-lactam free acid, eg., the N-tosyloxy or N-napsyloxy free acid.

Compounds represented by the formula 6 wherein A is —NHJ and J is the group —OC(O)R are prepared by coupling an acyl hydroxamate HONH—OC(O)R with the free acid represented by the formula 14.

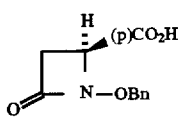

After removal of the benzyl group via catalytic hydrogenolysis, the N-hydroxy β-lactam product is reacted with an activated derivative of the acid which forms the leaving group, YOH, e.g., tosyl chloride. The coupling reaction is achieved with a water soluble carbodiimide such as 1-ethyl-3-(dimethylaminopropyl)carbodiimide hydrochloride in the presence of a base such as DMAP.

The compounds represented by the formula 6 wherein J is —P(O)(OR₁)(OR₁') are prepared with the same O-benzyl free acid represented by the formula 14 above.

A diphenylphosphoramide, or a mixed diphenylphosphoramide H₂NP(O)(OR₁)(OR₁') is coupled with the free acid using a water soluble carbodiimide, e.g., 1-ethyl-3-(dimethylaminopropyl)carbodiimide hydrochloride, and a base such as DMAP. After coupling the benzyl group is removed by hydrogenolysis and the N-hydroxy compound is treated with an activated form of the HOY free acid to provide the starting material represented by the formula 6.

Dialkylphosphoramides, e.g., J=—P(O)(OC₂H₅)₂ or mixed dialkylphosphoramides are best prepared by an alternate route. The free acid 14 is converted to an active ester, e.g., with ethyl chlorocarbonate and the active ester is allowed to react with sodium azide. The acid azide obtained is reacted with a trialkylphosphite yielding the acyl phosphinimine represented by the formula 15.

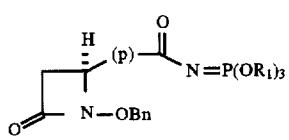

The latter intermediate is reacted promptly after preparation with dry hydrogen chloride in THF to yield the phosphoramide. Removal of the benzyl group as before and acylation of the N-hydroxy debenzylation product with an active derivative of the acid HOY provides the compound represented by the formula 6 wherein J is —P(O)(OR₁)(OR₁') wherein R₁ and R₁' are the same or different C₁–C₄ alkyl groups and Y has the same meanings as defined herein above.

Starting materials for the process represented by the formula 6 wherein J is —SO₂R₂ are prepared by coupling the sulfonamide, H2NSO₂R₂ with the free acid 14 using a water soluble carbodiimide and a base as described for the coupling reactions hereinabove. The coupled intermediate is debenzylated as described above and the Y group inserted as before to provide the compound 6 wherein J is —NHSO₂R₂ and R₂ is as defined herein above.

In a further specific embodiment of the invention the O-benzyl free acid (13) is coupled with tosylamide to yield the O-benzyl tosylamide (16).

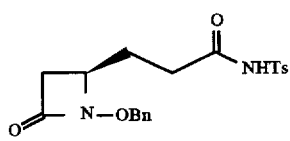

The benzyl group is removed catalytically with H₂ over Pd/C and the N-hydroxy product is acylated with tosyl chloride to yield (17).

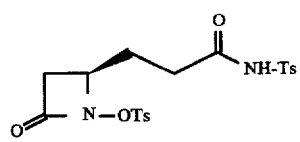

Cyclization of 17 in the process of the invention using 15 equivalents of DIEA in acetonitrile over about 2 days at about room temperature yielded (18) represented by the formula.

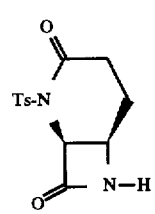

Other products identified in the reaction product mixture are represented by the formulas 18a, 18b, and 18c.

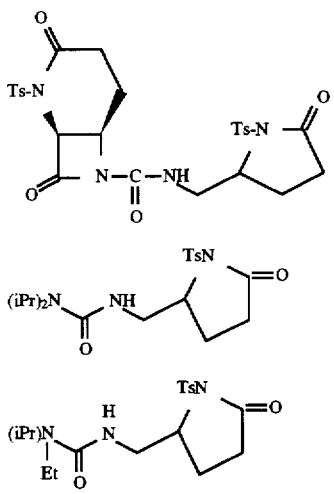

Examples of starting materials (formula 6) are shown in the following Table 1.

TABLE 1

| Y | p | A |
|---|---|---|
| tosyl | —CH$_2$— | OH |
| napsyl | —CH$_2$— | OH |
| tosyl | —CH$_2$CH$_2$— | OH |
| tosyl | —CH=CH— | OH |
| napsyl | —CH=CH— | OH |
| tosyl | —CH(CH$_3$) | OH |
| tosyl | —CH$_2$CH$_2$— | —NHSO$_2$C$_6$H$_5$ |
| tosyl | —CH$_2$CH$_2$— | —NH tosyl |
| napsyl | —CH$_2$CH$_2$— | NH napsyl |
| -P(O)(OC$_6$H$_5$)$_2$ | —CH$_2$CH$_2$— | —OH |
| -P(O)(OC$_6$H$_5$)$_2$ | —CH$_2$CH$_2$— | —NH tosyl |
| -P(O)(OC$_6$H$_5$)$_2$ | —CH$_2$CH$_2$— | —NH—P(O)(OC$_6$H$_5$)$_2$ |
| tosyl | —CH$_2$CH$_2$— | —NH—P(O)(OC$_6$H$_5$)$_2$ |
| napsyl | —CH$_2$CH$_2$— | —NH—P(O)(OC$_6$H$_5$)$_2$ |
| napsyl | —CH$_2$— | —NH—P(O)(OC$_2$H$_5$)$_2$ |
| napsyl | —CH$_2$— | —NH—P(O)(4—chlorophenoxy)$_2$ |
| napsyl | —CH$_2$— | —NH—P(O)(OC$_2$H$_5$)(OC$_6$H 5)$_2$ |
| napsyl | —CH$_2$— | —NH—P(O)(OC$_2$H$_5$)(OC$_6$H$_5$)$_2$ |
| tosyl | —CH$_2$— | —NH—OC(O) t-butyl |
| napsyl | —CH$_2$— | —NH—OC(O) t-butyl |
| C$_6$H$_5$SO$_2$ | —CH$_2$— | —NH—P(O)(OC$_6$H$_5$)$_2$ |
| (4-nitrophenyl) SO$_2$ | —CH$_2$— | —NH—P(O)(OC$_6$H$_5$)$_2$ |
| tosyl | —CH$_2$CH$_2$— | —NH—P(O)(OC$_6$H$_5$)$_2$ |

The compounds represented by the formula 1 are useful intermediates to both β-lactam antibiotics and to β-lactamase inhibitors. The diazabicyclo compounds provided by the invention (formula 1. Z=J—N=) may be hydrolyzed selectively to provide 3-substituted amino-4-(2-carboxyethyl) β-lactam compounds having the desired stereochemistry as shown below with a 6,4 bicyclo β-lactam.

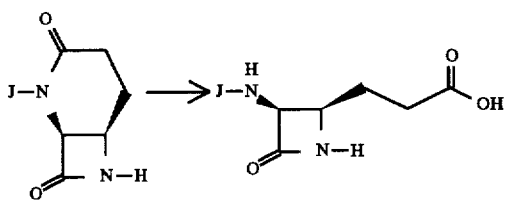

The hydrolysis product may be converted to a known 3-substituted carbacephem via known reaction routes.

The 5,4-diazabicyclo compounds likewise may be hydrolyzed to 3-substituted amino-4-carboxymethyl β-lactams as shown below.

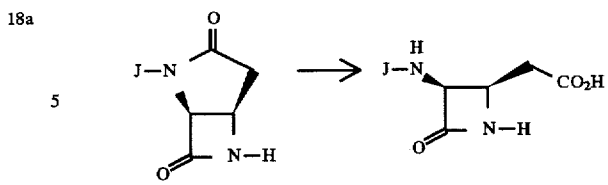

The 4-carboxymethyl group of the above hydrolysis product may be reduced to the 4-(2-hydroxyethyl) group and the latter halogenated to a 2-haloethyl substituted β3-lactam. The 4-(2-haloethyl) substituted 3-substituted amino azetidinone can be converted to a carbacephem antibiotic compound as provided by Munroe, U.S. Pat. No. 4,892,942.

Either of the 4-carboxymethyl or 4-(2-carboxyethyl) substituted β-lactams obtained in the hydrolysis of a compound of formula 1 can be converted to intermediates to known antibiotics or β-lactamase inhibitors according to Morin, U.S. Pat. No. 4,885,362.

The bicyclo β-lactam compounds where, in formula 1, Z is an oxygen atom also may be hydrolyzed to provide 3-hydroxy-substituted β-lactams having the desired stereochemistry.

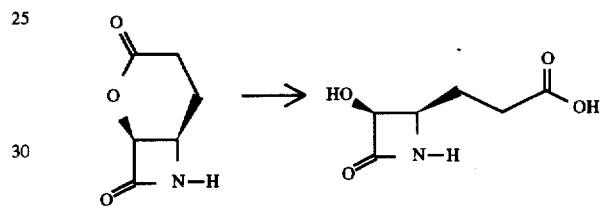

These hydrolysis products likewise may be converted to 7-hydroxycarbacephem compounds having the desired stereochemistry.

The compounds provided by the invention thus are useful in the preparation of a variety of β-lactam compounds having the stereochemistry required for biological activity. Accordingly, the invention provides a method for converting a 3-unsubstituted β-lactam to a 3-amino or 3-hydroxy substituted β-lactam having the stereochemistry of the biologically active antibiotics and β-lactamase inhibitors.

The compounds represented by the formula 1 also are converted to N-sulfo substituted compounds which can be used to inhibit β-lactamase, e.g. β-lactamase produced by Gram-negative bacteria. The enzyme inhibitors are prepared by treating a compound of the formula 1 with pyridine. SO$_3$ complex in an inert solvent or with DMF. SO$_3$ in DMF. See R. Charnas et al., EPO Publ. Appln. No. 0508234 p. 2.

The preparation of the N-sulfo compounds are illustrated by the following reaction scheme.

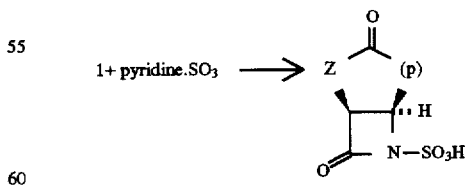

The product is best isolated in salt form, for example, an amine salt such as dicyclohexylamine, diethanolamine, or triethylamine or a sodium or potassium salt as obtained by ion exchange chromatography using Dowex 50X8.

The following Preparations and Examples are provided to further describe the compounds and process provided by the invention and are not to be construed as limitations thereof. Compound numbers have reference to the numbered compound formulas herein.

EXPERIMENTAL

General Methods. Melting points were taken on a Thomas-Hoover capillary melting point apparatus and are uncorrected. $^1$H NMR and $^{13}$C NMR spectra were obtained on a General Electric GN-300 spectrometer and were performed in chloroform-d. $^1$H NMR chemical shifts are reported in parts per million relative to tetramethylsilane. J values are given in hertz. For $^{13}$C NMR, reference was the center peak of chloroform-d (77.0 ppm). Infrared spectra were recorded on a Perkin-Elmer 1420 spectrophotometer. TF refers to thin film, and KBr refers to potassium bromide disk. Electron impact (EI) mass spectra, Chemical ionization (CI) mass spectra, and fast atom bombardment (FAB) were recorded on an AEI Scientific Apparatus MS 902 and Finnigan MAT Model 8430 spectrometers. Analytical TLC was carried out using commercially available aluminum-backed 0.2-mm silica gel 60 (230–400 mesh).

All reactions were periodically monitored by TLC and worked up after the complete consumption of starting material unless otherwise specified. Solvents for flash chromatography were distilled. Anhydrous methylene chloride, acetonitrile, triethylamine, and diisopropylethylamine were freshly distilled from $CaH_2$ and stored under nitrogen. All purchased reagents were of reagent grade quality and were used without further purification.

Preparation of Starting Materials

Preparation 1

2-Azetidinepropanoic acid, 1-(phenylmethoxy)-4-oxo (13) β-Lactam t-butyl ester 12 (1 g, 3.28 mmol) was dissolved in 1 mL of $CH_2Cl_2$ and cooled in an ice bath. Anisole (355 mL, 3.28 mmol), followed by trifluoroacetic acid (3 mL), was added and stirred for 2.5 h at 0° C. Toluene (15 mL) was added and the solvents were evaporated in vacuo. The residue was dissolved in 15 mL of ethyl acetate and extracted with three 10 mL portions of saturated $NaHCO_3$ solution. The combined aqueous layer was acidified to pH=2 by slow addition of 3M HCl. The aqueous layer was extracted with four 20 mL portions of $CH_2Cl_2$. The pooled organic extracts were dried over $Na_2SO_4$, filtered, and evaporated to give 619 mg (77%) of 13 as an oil. If the reaction was left for longer reaction times or higher temperatures, a by-product was formed which was not fully characterized but was carried throughout all of the extraction process and thus appeared to be a carboxylic acid. An analytical sample of acid 13 was obtained by recrystallization from ether-hexanes to yield colorless prisms: mp 62°–64° C.; TLC (ethyl acetate with 3 drops of acetic acid) $R_f$=0.35 (UV, PMA). $^1$H NMR δ7.39 (m, 5H), 4.96 (dd, 2H, AB system), 3.55 (m, 1H), 2.75 (dd, 1H, J=5.2, 13.8), 2.32 (dd, 1H, J=2.4, 13.8), 1.87–1.99 (m, 1H), 1.72–1.84 (m, 1H); $^{13}$C NMR δ177.53, 164.13, 135.03, 129.37, 129.12, 128.69, 78.27, 57.01, 37.55, 29.94, 27.37; $[\alpha]^{23}$=29.5° ($CHCl_3$, c=0.95); IR ($CCl_4$) 3700–2500 (br), 1775, 1750, 1710 cm$^{-1}$; HRMS (EI) Calcd for $C_{13}H_{15}NO_4$ 249.1001, Found: 249.1011.

Preparation 2

2-Azetidinepropanoic acid, 1-[[(4-methylphenyl) sulfonyl]oxy]-4-oxo (7) To a solution of 13 (57 mg, 0.23 mmol) in methanol (2.0 mL) was added 10% Pd on C and the solution was placed under a hydrogen balloon for 4 h. After filtration and concentration, the resultant N-hydroxy-β-lactam was used in the next reaction without further purification. To a solution of this N-hydroxy-β-lactam in $CH_3CN$ was added TsCl (43.6 mg, 0.23 mmol) and $Et_3N$ (0.064 mL, 0.46 mmol). After 10 min, $HO_2CCO_2H.2H_2O$ (28.8 mg, 0.23 mmol) was added to the reaction mixture. After 1 min, the reaction was concentrated under reduced pressure and the residue was purified by column chromatography with pure ethyl acetate as the eluent to yield 7 as an oily product (52 mg, 72.6%). $^1$H NMR δ1.96–2.05 (m, 1H), 2.11–2.26 (m, 1H), 2.47 (s, 3H), 2.48–2.53 (m, 3H), 2.90 (dd, $J_1$=6.0, $J_2$=14.5, 1H), 4.08–4.12 (m, 1H), 7.39 (d, J=8.0, 2H), 7.88 (d, J=8.4, 2H), 8.75 (b, 1H); $^{13}$C NMR δ21.8, 27.0, 29.6, 37.9, 58.8, 129.2, 130.0, 130.5, 146.6, 165.0, 177.7; IR (TF) 3650–2500 (br), 1800, 1710 cm$^{-1}$; MS (FAB) 314 (MH$^+$); MS (EI) 313 (M$^+$), 172, 155, 141, 97, 91; HRMS (FAB) MH$^+$ Calcd for $C_{13}H_{25}NO_6S$ 314.0698, Found: 314.0698.

Preparation 3

2-Azetidinepropanamide, N-(2,2-dimethyl-1-oxopropoxy)-1-(phenylmethoxy)-4-oxo. A solution of 13 (86 mg, 0.345 mmol) and O-pivaloylhydroxylamine hydrochloride (64 mg, 0.414 mmol) in a mixture of THF and $H_2O$ (25 mL, 1:1) was adjusted with 0.5N NaOH to pH=4.5. To the above solution was added EDC.HCl (240 mg, 1.24 mmol) divided into 6 portions (5 min for each portion). The reaction mixture was stirred at room temperature for 30 min over which time the pH of the solution was maintained at 4.5–5.0 with addition of either 0.5N NaOH or 1.5N HCl as needed. The solution was extracted with three 10 mL portions of ethyl acetate. The combined organic layers were washed with brine and dried over $MgSO_4$ and filtered. The dried solution was concentrated and the residue was purified by column chromatography with ethyl acetate/hexanes (1:1) to afford product as an oil (67 mg, 56%). $^1$H NMR δ1.31 (s, 9H), 1.86–1.99 (m, 2H), 2.22–2.27 (m, 2H), 2.31 (dd, $J_1$=2.2, $J_2$=13.8), 2.72 (dd, $J_1$=5.2, $J_2$=13.8, 1H), 3.64–3.68 (m, 1H), 4.95 (s, 2H) 7.38–7.39 (m, 5 H), 9.64 (b, 1H); $^{13}$C NMR δ26.9, 27.4, 28.1, 37.2, 38.1, 56.7, 78.0, 128.5, 129.0, 129.2, 134.7, 164.0, 169.4, 176.2; IR (TF) 3200, 2980, 1775, 1710, 1085 cm$^{-1}$; MS (CI with isobutane) 349 (MH$^+$).

Preparation 4

2-Azetidinepropanamide, N-(2,2-dimethyl-3-oxopropoxy)-1-[[(4-methylphlenyl)sulfonyl]oxyl]-4-oxo (8) A solution of the O-benzyl product of Preparation 3 (60 mg, 0.172 mmol) was hydrogenolyzed in methanol (3 mL) over Pd/C for 1 h. After filtration and concentration, the resultant N-hydroxy β-lactam was used for the next reaction without further purification. To a solution of this N-hydroxy β-lactam in $CH_2Cl_2$ (2 mL) was added TsCl (32.9 mg, 0.172 mmol) and $Et_3N$ (0.024 mL, 0.172 mmol). The reaction mixture was stirred at room temperature for 30 min. After concentration, the residue was purified by column chromatography with ethyl acetate/hexanes (1:1) to afford 8 as an oily product (37 mg, 52%). $^1$H NMR δ1.33 (s, 9H), 2.15–2.22 (m, 2H), 2.45–2.54 (m, 3H), 2.47 (s, 3H), 2.90 (dd, $J_1$=6.0, $J_2$=14.6), 4.14–4.20 (m, 1H), 7.39 (d, J=8.4, 2H), 7.89 (d, J=8.3, 2H); IR (TF) 3240, 2980, 1790, 1780, 1700, 1680 cm$^{-1}$; MS 413 (M$^+$H) 329, 296, 241, 184, 155, 137, 91; HRMS (FAB) MH$^+$ Calcd for $C_{18}H_{24}N_2O_7S$ 413.1382.

Preparation 5

2-Azetidinepropanamide, N-(triethoxyphosphorimidic)-1-(phenylmethoxy)-4-oxo. To a solution of 13 (80 mg, 0.32 mmol) in acetone (4.0 mL) was added Et$_3$N (0.05 mL, 0.35 mmol) and ethyl chloroformate (0.032 mL, 0.34 mmol) at 0° C. The reaction was finished within 30 min and formed the desired activated ester (monitored by TLC). To this reaction mixture was then added a solution of NaN$_3$ (31.4 mg, 0.48 mmol) in water (0.25 mL) at 0° C. The resulting suspension was left at 0° C. for 1 h. Then brine (0.5 mL) was added to this reaction mixture which was further extracted with three 0.5 mL portions of ethyl acetate. The combined organic layers were dried over MgSO$_4$ and concentrated to give the desired acyl azide as a colorless oil. Due to the instability of this compound, it was only partially characterized. $^1$H NMR δ1.74–1.93 (m, 2H), 2.27–2.36 (m, 3H), 2.74 (dd, J$_1$=5.2, J$_2$=13.7, 1H), 3.48–3.55 (m, 1H), 4.95–4.96 (d, 2H), 7.40 (s, 5H); IR (TF) 2940, 2140,1770, 1710, 1360,1180,1150.

To a solution of acyl azide in diethyl ether (2.0 mL) was added EtO$_3$P (0.082 mL, 0.48 mmol) at room temperature. This reaction mixture was warmed to reflux. Evolution of nitrogen was observed. After 30 min, the reaction was cooled down and was left at room temperature overnight. After concentration, the residue was purified by column chromatography, eluting with pure ethyl acetate, to afford product as an oil (83 mg, 63% from 13). $^1$H NMR δ1.32–1.37 (t, J=7.07, 9H), 1.73–1.85 (m, 1H), 2.03–2.12 (m, 1H), 2.29–2.38 (m, 3H), 2.70 (dd, J$_1$=5.2, J$_2$=13.6, 1H), 3.63–3.69 (m, 1H), 4.13–4.23 (q, J=7.1, 6H), 4.93 (d, J=10.9, 1H), 4.99 (d, J=10.9, 1H), 7.35–7.43 (m, 5H); IR (TF) 2980, 1770, 1615 cm$^{-1}$; MS 412 (M$^+$), 354, 305, 263, 208, 183, 180, 152, 124, 91.

Preparation 6

2-Azetidinepropanamide, N-(diethoxyphosphoramidic)-1-(phenylmethoxy)-4-oxo. N-Acyl phosphinimine of Preparation 5, (50 mg) was dissolved in dry THF (10 mL). Through this solution was passed dry HCl (generated from dehydration of an HCl solution by concentrated H$_2$SO$_4$). The reaction took only a few seconds (quickly monitored by TLC). Then the solvent was evaporated and the residue was added to a saturated solution of KHCO$_3$. This solution was then extracted with three portions of ethyl acetate and the combined organic solution was washed with brine once. The organic solution was dried and then concentrated to yield product as a colorless oil (40 mg, 86%). $^1$H NMR δ1.32–1.37 (t, J=7.0, 6H), 1.73–1.85 (m, 1H), 2.01–2.12 (m, 1H), 2.29–2.38 (m, 2H), 2.67–2.74 (dd, J$_1$=5.2, J$_2$=13.6, 1H), 3.62–3.69 (m, 1H), 4.13–4.23 (m, 4H), 4.92–4.95 (d, J=10.9, 1H), 4.97–5.01 (d, J=11.0, 1H), 7.35–7.43 (m, 5H), 9.00 (b, 1H); $^{13}$C NMR δ16.0 (d, J$_{C-P}$=6.7), 27.2, 32.3 (d, J$_{C-P}$=9.5), 37.5, 56.8, 64.1 (d, J$_{C-P}$=6.7), 78.1, 128.5, 128.6, 128.9, 129.2, 135.0, 163.9, 173.4 (d, J$_{C-P}$=4.0); IR (TF) 3120, 2980, 1770, 1710 cm$^{-1}$; MS 384 (M$^+$), 262, 234, 220, 195, 180, 155 (base peak), 146, 127; HRMS Calcd for C$_{17}$H$_{25}$N$_2$O$_6$P 384.1450, Found: 384.1468.

Preparation 7

2-Azetidinepropanamide, N-(triethoxyphosphoramidic)-1-[[(4-methylphenyl)sulfonyl]oxy]-4-oxo. A solution of compound Preparation 6 (40 mg, 0.1 mmoL) was subjected to hydrogenolysis for 3 h according to the general procedure. The resultant N-hydroxy β-lactam was dissolved in CH$_2$Cl$_2$. To the above solution was in turn added TsCl (14 mg, 0.07 mmoL) and triethylamine (0.01 mL, 0.07 mmoL). The reaction mixture was stirred for 10 min. After concentration, the residue was purified by column chromatography with pure ethyl acetate as the eluent to afford product as an oil (24 mg, 55%). $^1$H NMR δ1.35–1.39 (t, J=7.1, 6H), 2.01–2.18 (m, 1H), 2.20–2.25 (m, 1H), 2.47 (s, 3H), 2.48–2.55 (m, 2H), 2.87 (dd, J$_1$=6.0, J$_2$=14.5, 1H), 4.08–4.17 (m, 1H), 4.18–4.29 (m, 4H), 7.38 (d, J=8.2, 2H), 7.88 (d, J=8.3, 2H), 8.86 (b, 1H); $^{13}$C NMR δ16.0, 16.1, 21.8, 27.0, 32.2, 32.3, 37.9, 59.0, 64.2, 64.3, 129.1, 130.0, 130.3, 146.5, 165.0, 173.4; IR (TF) 3230, 2985, 2920, 1800, 1710 cm$^{-1}$.

Preparation 8

2-Azetidinepropanamide, N-(diphenoxyphosphoramidic)-1-(phenylmethoxy)-4-oxo A mixture of compound 13 (269 mg, 1.08 mmol), diphenylphosphoramide (207 mg, 0.83 mmol), 4-dimethylaminopyridine (158 mg, 1.30 mmol), EDC.HCl (248 mg, 1.30 mmol) were dissolved CH$_2$Cl$_2$ (7.0 mL). After stirring for 15 min, another portion of diphenylphosphoramide (104 mg, 0.42 mmol) was added to the solution. The color of the reaction changed from colorless to yellow within 40 min and at the same time became homogeneous. After 1 h and 20 min, more EDC.HCl (200 mg, 1.0 mmol) was added to the yellow solution. The reaction mixture was left at room temperature for a total of 40 h. The solvent was evaporated and the residue was purified by column chromatography with ethyl acetate/hexanes (3:1) to afford product as a colorless oil (314 mg, 61%) $^1$H NMR δ1.64–1.73 (m, 1H), 1.79–1.90 (m, 1H), 2.14–2.24 (m, 3H), 2.58 (dd, J$_1$=5.2, J$_2$=13.7, 1H), 3.39–3.46 (m, 1H), 4.86 (d, J=11.1, 1H), 4.92 (d, J=11.1, 1H), 7.16–7.40 (m, 15H), 9.20 (b, 1H); $^{13}$C NMR δ27.07, 32.5 (d, J$_{C-P}$=9.69), 37.38, 56.64, 78.04, 120.17, 120.27, 120.32, 125.08, 125.73, 128.58, 128.96, 129.25, 129.67, 129.76, 134.96, 149.84 (d, J$_{C-P}$=6.5), 163.85, 172.90 (d, J=3.36); IR (TF) 3120, 3070, 3040, 2930, 1770, 1720 cm$^{-1}$; MS 480 (M$^+$), 436, 341, 281, 251 (base peak), 173, 146; HRMS FAB MH$^+$ Calcd for C$_{25}$H$_{25}$N$_2$O$_6$P 481.1529, Found: 481.1528.

Preparation 9

2-Azetidinepropanamide, N-(diphenoxyphosphoramidic)-1-[[(4-methylphenyl)sulfonyl]oxy]-4-oxo (10) The product of Preparation 8 (304 mg, 0.63 mmol) in methanol (10 mL) was subjected to hydrogenolysis for 2 h according to the general procedure. The resultant oil was dissolved in CH$_2$Cl$_2$ (5.0 mL). To this solution was added TsCl (120.7 mg, 0.63 mmol) and TEA (0.088 mL, 0.63 mmol). After 40 min, the solvent was removed and the residue was purified by column chromatography (ethyl acetate/hexanes 3:1) to yield the desired product as a colorless oil (302 mg, 87%). $^1$H NMR δ1.83–1.95 (m, 1H), 2.09–2.16 (m, 1H), 2.31–2.37 (m, 3H), 2.43 (s, 3H), 2.70 (dd, J$_1$=6.0, J$_2$=14.5, 1H), 3.88–3.92 (m, 1H), 7.19–7.35 (m, 12H), 7.85 (d, J=8.4, 2H), 9.20 (b, 1H); $^{13}$C NMR δ21.4, 26.4, 32.0 (d, J$_{C-P}$=10.3 Hz), 37.3, 58.5, 120.0 (d, J$_{C-P}$=4.7), 125.5, 128.8, 129.4, 129.6, 129.8, 130.0, 146.3, Preparation 10

2-Azetidinepropanamide, N-[(4-methylphenyl)sulfonyl]-1-(phenylmethoxy)-4-oxo (16). β-Lactam carboxylic acid 13 (135 mg, 0.542 mmol) was dissolved in CH$_2$Cl$_2$ (4 mL) and then tosylamide (96 mg, 0.558 mmol), dimethylaminopyridine (70 mg, 0.369 mmol), and EDC.HCl (125 mg, 0.651 mmol) were added. The reaction was stirred for 2 days at room temperature and the color of the solution turned yellow. Ethyl acetate (15 mL) was added and the organic layer was washed three times with 5 mL of 0.5M HCl and once with 5 mL of brine. The organic layer was dried over MgSO$_4$, filtered and evaporated to give 223 mg of an oil. Column chromatography, eluting with ethyl acetate, gave 185 mg (85%) of an analytical sample as a sticky glass.

$R_f$=0.46 (UV, PMA, ethyl acetate); $^1$H NMR δ9.04 (br s, 1H), 7.93 (d, 2H, J=8.1 Hz), 7.34 (7H, benzyl and sulfonate doublet overlapped), 4.91 (d, 1H, J=11.1 Hz), 4.86 (d, 1H, J=11.1 Hz), 3.53 (m, 1H), 2.65 (dd, 1H, J=13.8, 5.1 Hz), 2.42 (s, 3H), 2.18–2.38 (m, 3H), 1.79 (m, 2H); $^{13}$C δ170.20, 164.29, 145.04, 135.68, 134.75, 129.58, 129.35, 129.13, 128.69, 128.27, 78.18, 56.80, 37.11, 31.44, 26.33, 21.66; IR (TF) 3200 br, 1770 s, 1750 s, 1715 s cm$^{-1}$; [a]$_D$=15° (CHCl$_3$, c=1); HRMS: (ammonia CI). Calcd M$^+$NH$_4$ 420.15932. Found: 420.1613.

Preparation 11

2-Azetidinepropanamide, N-[(4-methylphenyl)sulfonyl]-1-[[(4-methylphenyl)sulfonyl]oxyl]-4-oxo (17) N-Acylsulfonamide 16 (527 mg, 1.31 mmol) was dissolved in methanol (12 mL) and 10% Pd on carbon (180 mg) was added and the solution was placed under a hydrogen balloon. After 30 minutes TLC analysis (ethyl acetate) showed reaction completion. The starting material had an $R_f$=0.48 (UV, PMA), and the product N-hydroxy β-lactam an $R_f$=0.15 (UV, PMA). The Pd catalyst was removed by filtration through celite which was subsequently rinsed several times with ethyl acetate. The combined solvent was removed by rotary evaporation to leave a white foam which was dissolved in 15 mL of CH$_2$Cl$_2$. Tosyl chloride (247 mg, 1.3 mmol) and triethylamine (181 mL, 1.3 mmol) were added sequentially to this solution. A small amount of gas evolved. After 20 min, TLC analysis (ethyl acetate) showed the product ($R_f$=0.50 UV, PMA) and tosyl chloride $R_f$=0.64 (UV). The solvent was evaporated and the residue was dissolved in a minimal amount of CHCl$_3$ and placed on a silica gel column and eluted with 3:1 ethyl acetate:hexanes. After evaporation of the pooled fractions 465 mg (78%) of 17 as a foam was obtained. $^1$H NMR δ9.23 (br s, 1H), 7.94 (d, 2H, J=8.4), 7.85 (d, 2H, J=8.4), 7.3–7.41 (m, 4H), 3.98 (m, 1H), 2.81 (dd, 1H, J=6, 14.4), 2.35–2.45 (m, 9H), 1.9–2.1 (m, 2H); IR 3220 br, 1795 s, 1725 s, 1595 m, 1370, 1190, 1170 cm$^{-1}$; MS (FAB) MH$^+$=467.

EXAMPLE 1

2-Oxa-7-azabicyclo [4.2.0] octane, 3,8-dioxo (2): To a solution of 7 (213 mg, 0.68 mmol) in CH$_3$CN (22 mL) was added DIEA (0.24 mL, 1.36 mmol). The reaction mixture was left for 60 h at room temperature (monitored by TLC) and then passed through a plug of silica gel to remove salts and any polar impurities. The clear oil contained mainly desired product 2 and by-product 2a in a ratio of 1:2 (by $^1$H NMR analysis). These products were further purified by column chromatography with pure ethyl acetate to a yield colorless oil (49 mg, 51% combined yield. Note that these two products were isographic on TLC. This made the complete separation of the two products by column chromatography difficult). $^1$H NMR δ2.02–2.10 (m, 1H), 2.23–2.30 (m, 1H), 2.64–2.70 (m, 2H), 4.19 (t, J=4.3, 1H), 5.39 (dd, J$_1$=2.2, J$_2$=5.2, 1H), 6.05 (b, 1H); IR (TF) 3300, 2985, 2940, 1760–1790 cm$^{-1}$; MS (CI with isobutane), MH$^+$142; HRMS (FAB) MH$^+$ Calcd for C$_6$H$_7$NO$_3$ 142.0504, Found: 142.0507. By-product 2a $^1$H NMR δ1.90–2.71 (m, 8H), 3.35–3.52 (m, 1H), 3.65–3.79 (m, 1H), 4.58 (t, J=3.1, 1H), 4.63–4.69 (m, 1H), 5.47 (d, J=5.7, 1H), 6.81 (b, 1H); IR (TF) 3360, 2980, 1760–1785, 1695, 1530 cm$^{-1}$; MS (FAB) MH$^+$283, 243, 229.

EXAMPLE 2

2,7-Diazabicyclo [4.2.0] octane, 3,8-dioxo-2-(2,2-dimethyl-1-oxopropoxy) (9) and 2-Oxa-7-azabicyclo [4.2.0] octane, 3-[imino(2,2-dimethyl-1-oxo-propoxy)]-8-oxo (9a) To a solution of 8 (64 mg, 0.15 mmol) in CH$_3$CN (10 mL) was added DIEA (0.054 mL, 0.3 mmol). The reaction mixture was left at room temperature for 60 h and turned brown. After concentration under reduced pressure, the residue was purified by column chromatography with ethyl acetate to yield a mixture of 9 and 9a as white solids (11 mg, 30%). $^1$H NMR spectrum indicated the ratio of 9 to 9a was 1:1. These two products could only be enriched from each other through column chromatography. Compound 9: $^1$H NMR δ1.33 (s, 9H), 2.05–2.16 (m, 2H), 2.57–2.62 (m, 2H), 4.38–4.41 (m, 1H), 4.74 (dd, J$_1$=1.7, J$_2$=5.7, 1H), 5.86 (b, 1H); IR (TF) 3280, 2980, 1775, 1765, 1685; MS 197 (M$^+$–43), 156, 113, 57; HRMS (FAB) MH$^+$ Calcd for C$_{11}$H$_{16}$N$_2$O$_4$ 241.1188, Found 241.1200. Compound 9a: Mp 163°–167° C. (dec.). $^1$H NMR δ1.27 (s, 3H), 1.96–2.06 (m, 1H), 2.22–2.30 (dtd, J$_1$=14.8, J$_2$=3.6, J$_3$=1.2, 1H), 2.68–2.71 (m, 2H), 4.21–4.25 (m, 1H), 5.29 (dd, J$_1$=2.0, J$_2$=5.3, 1H), 5.92 (b, 1H); IR (TF) 3240, 2980, 2880, 1755–1780, 1645 cm$^{-1}$; MS 241, 157, 57; HRMS FAB MH$^+$ Calcd for C$_{11}$H$_{16}$N$_2$O$_4$ 241.1188, Found 241.1191.

The conversion of (9a) to (2). To a solution of 9a (5 mg) in a mixture of ether (1.0 mL), ethyl acetate (1.0 mL) and chloroform (0.5 mL) was added 3 drops of HCl (1M in H$_2$O). This reaction mixture was stored at 0° C. overnight and then dried over MgSO$_4$. $^1$H NMR spectrum of the concentrated reaction revealed a clean mixture of 9a and 2 in a ratio of 1:1.

EXAMPLE 3

2,7-Diazabicyclo[4.2.0] octane, 3,8-dioxo-2-(diphenoxyphosphoramide) (11) Compound 10 (297 mg, 0.546 mmol) was dissolved in CH$_3$CN (20.0 mL). To this solution was added DIEA (0.19 mL, 1.09 mmol). The reaction mixture was stirred at room temperature for 46 h. The solvent was evaporated under vacuum and the residue was purified by column chromatography (ethyl acetate/hexanes 3:1) to yield the desired product as a colorless oil (67 mg, 33%). From the above reaction mixture were also isolated diphenylphosphoramide (13.0 mg) and N-(4-oxopentanoyl) diphenylphosphoramide (8 mg). Data for 11: $^1$H NMR δ1.41–1.53 (m, 1H), 2.05–2.13 (m, 1H), 2.50–2.63 (m, 2H), 4.06–4.09 (m, 1H), 5.55 (ddd, J$_1$=0.6, J$_2$=5.8, J$_3$=10.2, 1H), 5.76 (b, 1H), 7.20–7.38 (m, 10H); $^{13}$C NMR δ23.9, 28.4–28.5 (J=5.9), 47.3–47.4 (J=4.3), 62.6 (J=1.3), 120.25, 120.35, 120.41, 120.43, 120.47, 120.49, 125.6, 125.9, 129.7, 129.8, 149.7, 149.76, 149.78, 149.9, 166.5, 172.7; IR (TF) 3250, 1770, 1710 cm$^{-1}$; MS 372 (M$^+$), 329 (base peak), 316, 277, 236, 173, 91; HRMS Calcd for C$_{18}$H$_{17}$N$_2$O$_5$P 372.08751, Found: 372.0872. Data for N-(4-oxo-pentanoyl) diphenylphosphoramide. $^1$H NMR δ2.18 (s, 3H), 2.53–2.57 (t, 1H, J=5.9), 2.71–2.75 (t, J=6.5), 7.21–7.37 (m, 10H), 7.87 (b, 1H); IR (TF) 3140, 2920, 1720, 1590 cm$^{-1}$; MS 347 (M$^+$), 333, 332, 276, 254, 251, 240, 175, 121, 94, 77.

EXAMPLE 4

2,7-Diazabicyclo [4.2.0] octane, 3,8-dioxo-2-[(4-methylphenyl)sulfonyl]Intramolecular Cyclization of (17). N-Tosyloxy-β-lactam 17 (500 mg, 1.07 mmol) was dissolved in acetonitrile (50 mL) and DIEA (2.8 mL, 16.05 mmol, 15 eq.) was added. After two days, the solvent was evaporated and the residue was dissolved in ethyl acetate (75 mL) and washed with two 10 mL portions of 0.5M HCl, once with 15 mL of saturated NaHCO$_3$ solution, dried over MgSO$_4$, filtered, and evaporated to give 180 mg of residue.

Column chromatography with 3:1 ethyl acetate in hexanes gave 37 mg (12%) of 18 10 mg (4%) of 18a, 49 mg (12%) of 18b, and 11 mg (3%) of 18c after evaporation of the pooled fractions.

2,7-]Diazabicyclo [4.2.0] octane, 3,8-dioxo-2-[(4-methylphenyl)sulfonyl](18). Recrystallized from CH$_2$Cl$_2$/hexanes Mp 192°–194° C. dec. R$_f$=0.33 ethyl acetate (UV, PMA slight blue). $^1$H NMR δ8.07 (d, 2H, J=8.4), 7.34 (d, 2H, J=8.4), 5.93 (br s NH, 1H), 5.89 (dd, 1H, J=5.4, 0.6), 4.38 (t, 1H, J=3.9), 2.43 (s, 3H), 2.4–2.5 (m, 1H), 2.15–2.22 2.22 (m, 1H), 1.9–2.05 (m, 2H); $^{13}$C NMR δ169.16, 165.36, 145.26, 135.11, 129.33, 128.33, 61.80, 48.44, 28.72, 24.04, 21.71; IR (TF) 3450 br, 1770 s, 1700, 1350, 1170 s cm$^{-1}$; [a]$_D$=−132° (CHCl$_3$, c=0.28); MS (EI) gave M$^+$=294, CI (isobutane) gave MH$^+$=295, HRMS MNH$_4^+$ (ammonia CI) Calcd for C$_{13}$H$_{14}$N$_2$O$_4$S 312.1018, Found: 312.1032.

Characterization data for (18a). R$_f$=0.43 (ethyl acetate). $^1$H NMR δ8.03 (d, 2H, J=8.4), 7.90 (d, 2H, J=8.4), 7.3–7.4 (t, 4H), 6.78 (t, 1H, J=6.3), 5.96 (d, 1H, J=6.6), 4.78 (m, 1H), 4.51 (m, 1H), 3.63 (dt, 1H, J=1.8, 6), 2.5–2.7 (m, 2H), 2.44 (s, 3H), 2.43 (s, 3H), 2.1–2.4 (m, 4H), 1.9–2.0 (m,2H); IR 3360 br, 1775, 1710, 1355, 1165 cm$^{-1}$; HRMS (FAB) MH$^+$ Calcd for C$_{26}$H$_{28}$N$_4$O$_8$S$_2$ 589.1428, Found: 589.1426.

Characterization data for (18b). R$_f$=0.37 (ethyl acetate). $^1$H NMR δ7.98 (d, 2H, J=8.4), 7.35 (d, 2H, J=8.4), 4.45 (m, 2H), 3.55–3.89 (m, 4H), 2.44 (s, 3H), 2.10–2.35 (m, 2H), 1.12 (dd, 12H, J=2.7, 6.9); $^{13}$C NMR δ174.19, 156.96, 145.27, 135.53, 129.67, 128.42, 61.04, 45.27, 43.64, 31.14, 23.35, 23.09, 21.68, 21.26, 21.22 (Note that both $^1$H and $^{13}$C NMR spectra contain diastereotopic isopropyl groups); IR 3450 br, 3350 br, 1735 s, 1625, 1510, 1350, 1160, 665 cm$^{-1}$; [a]$_D$=−50.7° (CHCl$_3$, c=0.6); HRMS (FAB) MH$^+$ Calcd for C$_{19}$H$_{29}$N$_3$O$_4$S 396.1957, Found: 396.1950.

Characterization for (18c). Compound 18c was not isolated pure but the $^1$H NMR resembled that of compound 18a R$_f$=0.25 (ethyl acetate). IR neat oil 3450, 1745–1730, 1625, 1165 cm$^{-1}$; MS (FAB) MH$^+$ Calcd for C$_{18}$H$_{27}$N$_3$O$_4$S 382, Found: 382.

EXAMPLE 5

2,6-Diazabicyclo[3.2.0]heptane, 3,7-dioxo-2-(diphenoxyphosphoramide). By following the procedures and conditions described by Example 3, 1-azetidineacetamide, N-(2,2-dimethyl-3-oxopropoxy)-1-{[(2-naphthyl)sulfonyl]oxy}-4-oxo, is treated in acetonitrile with DIEA to provide the Title compound.

EXAMPLE 6

2-Oxa-6-azabicyclo[3.2.0]heptane, 3,7-dioxa (3). In accordance with Example 1, 1-azetidine acetic acid, 1-{[(4-methylphenyl)sulfinyl]oxy}-4-oxo, is treated in propionitrile with DIEA to form compound (3).

We claim:

1. A compound of the formula

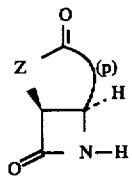

wherein Z is =N—J, wherein J is —OC(O)R, —P(O)(OR$_1$)(OR$_1$') or —SO$_2$R$_2$, wherein R is C$_1$–C$_4$ alkyl, R$_1$ and R$_1$' independently are C$_1$–C$_4$ alkyl, phenyl or substituted phenyl; R$_2$ is C$_1$–C$_4$ alkyl, phenyl, substituted phenyl, naphthyl or substituted naphthyl; and p is —CH$_2$—, —CH$_2$CH$_2$—, cis-CH=CH—, —CH(alk)—, —CH$_2$—CH(alk), or —CH(alk)CH$_2$—, wherein alk is methyl or ethyl.

2. The compound of claim 1 wherein p is —CH$_2$— or —CH$_2$CH$_2$—.

3. The compound of claim 2 wherein J is —O(CO)R or —P(O)(OR$_1$)(OR$_1$').

4. The compound of claim 3 said compound being 2,7-diazabicyclo[4.2.0]octane, 3,8-dioxo-2-(2,2-dimethyl-1-oxopropoxy).

5. The compound of claim 3 said compound being 2,7-diazabicyclo[4.2.0]octane, 3,8-dioxo-2-(diphenoxyphosphoramide).

6. The compound of claim 2 wherein J is —SO$_2$R$_2$.

7. The compound of claim 6 said compound being 2,7-diazabicyclo[4.2.0]octane, 3,8-dioxo-2-[(4-methylphenyl)sulfonyl].

* * * * *